United States Patent
Devine

(10) Patent No.: US 8,221,681 B2
(45) Date of Patent: Jul. 17, 2012

(54) METHOD AND APPARATUS FOR DECONTAMINATION OF TUBING

(75) Inventor: Steven T. Devine, Rockaway, NJ (US)

(73) Assignee: Camfil Farr, Inc., Riverdale, NJ (US)

( * ) Notice: Subject to any disclaimer, the term of this patent is extended or adjusted under 35 U.S.C. 154(b) by 162 days.

(21) Appl. No.: 12/545,163

(22) Filed: Aug. 21, 2009

(65) Prior Publication Data
US 2011/0044853 A1 Feb. 24, 2011

(51) Int. Cl.
*A61L 2/16* (2006.01)
(52) U.S. Cl. ............................. 422/28; 422/33; 95/278
(58) Field of Classification Search ............... 422/28, 422/33; 95/278
See application file for complete search history.

(56) References Cited

U.S. PATENT DOCUMENTS

| | | | |
|---|---|---|---|
| 6,454,871 B1 * | 9/2002 | Labib et al. ............... | 134/8 |
| 2005/0013726 A1 | 1/2005 | Hill et al. | |
| 2006/0042359 A1 | 3/2006 | Morse et al. | |
| 2006/0272301 A1 | 12/2006 | Morse et al. | |
| 2007/0044438 A1 | 3/2007 | Morse et al. | |
| 2009/0056547 A1 | 3/2009 | Huza et al. | |

OTHER PUBLICATIONS

PCT international search report and written opinion of PCT/US 10/46087 dated Jan. 27, 2010.

* cited by examiner

*Primary Examiner* — Sean E Conley
(74) *Attorney, Agent, or Firm* — Patterson & Sheridan, LLP

(57) ABSTRACT

Embodiments of the invention generally provide an apparatus and method for decontaminating tubing. The invention is particularly suitable for decontaminating tubing in a test system used for certifying a filter in a containment system. In one embodiment, a test system for a containment system is provide that includes a sample system including equipment adapted for testing a filter disposed in a containment system utilizing samples obtained from a downstream sample port and a upstream sample port of the containment system, and a device for reversing a flow within the sample system. In another aspect of the invention, a method for decontaminating tubing is provided. In another embodiment, the method includes flowing a sterilization agent through tubing in a first direction and flowing the sterilization agent through tubing in a second direction.

17 Claims, 10 Drawing Sheets

FIG. 5

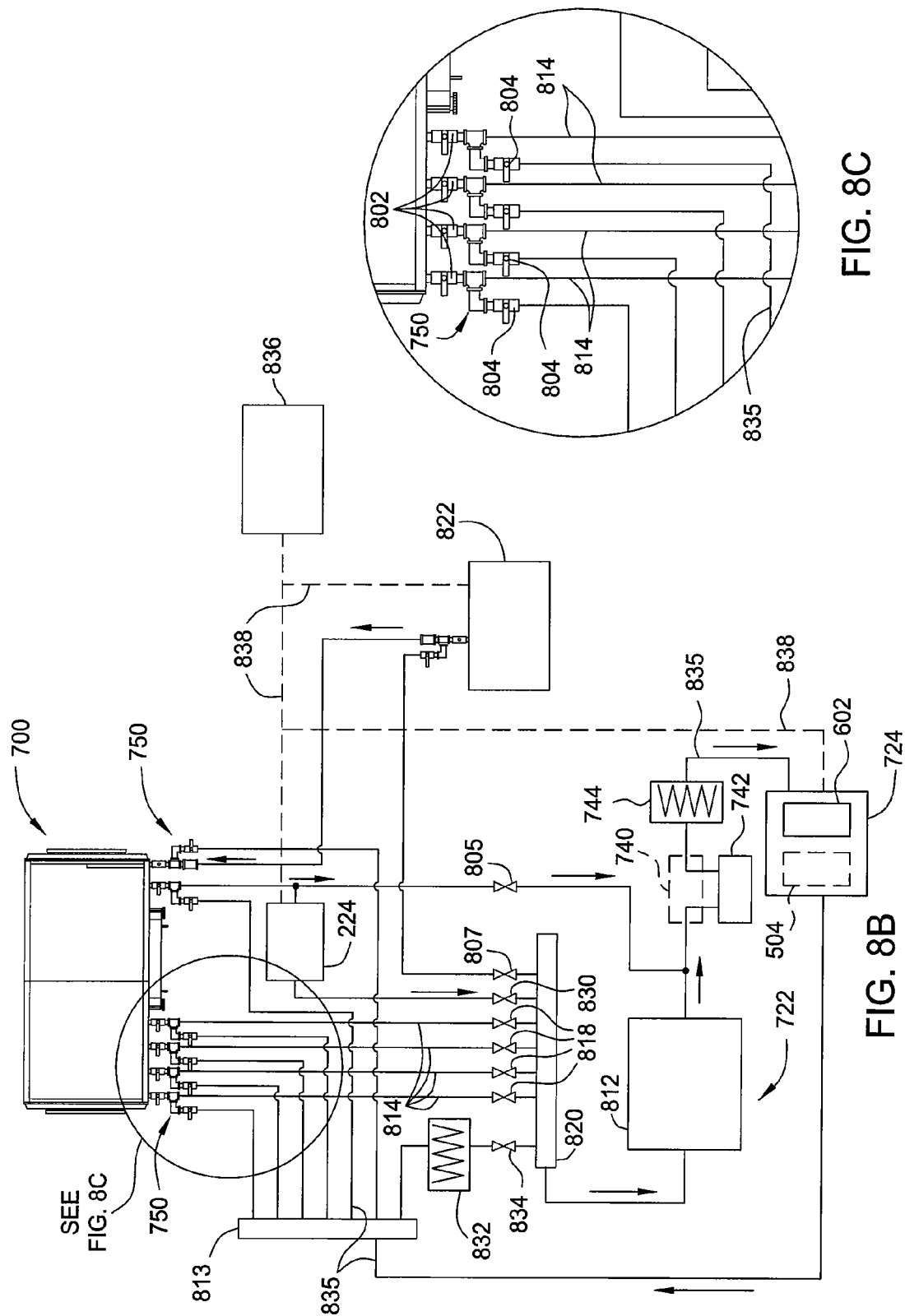

METHOD AND APPARATUS FOR DECONTAMINATION OF TUBING

CROSS-REFERENCE TO RELATED APPLICATIONS

This application is related to U.S. patent application Ser. No. 12/163,384, filed on Jun. 27, 2008, which is incorporated by reference in its entirety.

BACKGROUND OF THE INVENTION

1. Field of the Invention

The embodiments described herein generally relate to an apparatus and method for decontaminating tubing using an aerosol, vapor or gaseous decontamination or sterilization agent, and more particularly, embodiments described herein relate to a system and method for decontaminating a containment system and containment filter testing system.

2. Description of the Related Art

Numerous facilities handle hazardous and potentially fatal compounds and/or particles. These facilities include, for example, biological safety labs, pharmaceutical manufacturing facilities, biotechnology research labs, and production facilities. The hazardous particulates may include anything that is harmful or fatal to humans including, but not limited to, viruses, bacteria, chemicals, and waste products. Typically a containment system in the facility prevents the hazardous particles from escaping from the facility by filtering the air exiting hazardous areas prior to entering the surrounding environment.

The containment system typically consists of multiple components arranged in series. The components generally include one or more filter housing sections, one or more filters disposed in the one or more filter housing sections, an upstream test section, a downstream test section, and an air tight damper for isolating the containment system from the upstream and downstream ductwork that the containment system is coupled thereto.

The performance of the filters disposed in the containment system is critical to prevent human exposure to the hazardous particles. Therefore, it is necessary to certify the performance (e.g., leak and/or filtration efficiency) of the filters on a regular basis. The certification process ensures that the filters are meeting predefined operations criteria and/or standards. In-situ filter certification is often required for filters handling hazardous particles after the filters installation into the contamination housing. In-situ filter testing is performed by injecting an aerosol challenge upstream of the filter at a known concentration, flowing the aerosol laden air through the filter typically at an operational flow rate, and sampling the air downstream of the filter to determine at least one of a leak (such as pin-hole or edge) or an overall filtration efficiency of the filter based on a predefined filtering performance criteria.

There are two current methods for in-situ certification of a containment system. The first method uses two by-pass ports on the containment housing. A first port is upstream of the filter and a second port is located downstream from the filter. These ports are normally closed. To certify the filters, the containment system is turned off causing the facility to be shut down. The upstream and downstream dampers are closed while the inside of the containment housing is decontaminated by exposure to a decontamination agent. The ports are then opened to allow access to the filter during testing of the filter. The downstream damper and exhaust may be opened to allow the air and aerosol to pass through the filter. Since the containment system has been decontaminated and isolated from the upstream duct work, it is safe to test the filter in the containment system while allowing the air to flow through the exhaust and into the environment.

The second method for in-situ certification of the containment system uses air from the facility. This method requires both the laboratory and the containment housing be decontaminated prior to filter testing. During decontamination, the upstream and downstream dampers of the housing must be closed. When decontamination is complete the dampers open thereby allowing air from the lab or other work area into the containment system. An aerosol challenge is introduced into the air flowing through the filter to facilitate testing of the filter.

The methods described above are costly and time consuming. The testing process requires the facility and/or the containment system to be shut down during filter testing. The shutdown and decontamination may take several hours and even days in some cases. Ongoing research may need to be stopped temporarily or abandoned altogether. Moreover, it is difficult to effectively decontaminate the entire network of tubing utilized to test the filter disposed within the containment system. Thus, higher concentrations of decontaminant agents or longer soak times must be utilized in order to ensure a safe environment. The loss of time of the facility during a decontamination cycle may cost the facility millions of dollars due to lost research time or production time.

Therefore, there is a need for an improved method and apparatus for conducting decontamination and testing a filter in a containment system.

SUMMARY OF THE INVENTION

Embodiments of the invention generally provide an apparatus and method for decontaminating tubing and small spaces. The invention is particularly suitable for decontaminating tubing in a test system used for certifying a filter in a containment system. It is well understood and documented that proper environmental conditions must exist in order to obtain effective decontamination of a space and the surface that exist within or enclose that space. The proper temperature, relative humidity, agent concentration and exposure to the sterilization/decontamination agent must be provided. Because of the existence of relatively long tubes, restrictions, valves, orifices, pumps, filters and other complex surfaces and spaces in the system and because of the development of both high and low pressure regions, turbulence and dead zones when there is flow in the system, it is not reliably possible to provide adequate environmental conditions to assure decontamination in every part of the system in a normal running mode. Embodiments of the invention include apparatus and methods that compensate for and overcome these limitations resulting in overall conditions adequate for acceptable decontamination.

In one embodiment, a test system for a containment system is provide that includes a sample system including equipment adapted for testing a filter disposed in a containment system utilizing samples obtained from a downstream sample port and a upstream sample port of the containment system, and a device for reversing a flow within the sample system.

In other embodiments, the test system may include at least one of a reversible vacuum pump; at least one valve having a first state that allows flow from the sample system into a vacuum pump, the flow causing a first directional flow within the sample system, and a second state that prevents flow from the sample system into the vacuum pump, the at least one valve also allowing a second directional flow through the sample system that is opposite of the first directional flow; and at least one valve having a first state that couples the inlet of a vacuum pump to the sample system and a second state that couples an outlet of the vacuum pump to the sample system.

In another aspect of the invention, a method for decontaminating tubing is provided. In another embodiment, the method includes flowing a sterilization or decontamination agent through tubing in a first direction and flowing the agent through tubing in a second direction.

In another embodiment, a method for decontaminating tubing in a test system coupled to a containment system is provided that includes operating a vacuum pump to create a flow of sterilization or decontamination agent in a test system in a first flow direction, the test system coupled to the containment and configured to test a filter therein, and reversing the flow direction of the agent in the test system.

BRIEF DESCRIPTION OF THE DRAWINGS

The accompanying drawings, which are incorporated in and constitute a part of the specification, schematically illustrate the present invention, and together with the general description given above and the detailed description given below, serve to explain the principles of the invention.

FIG. 5 depicts a section view of the containment system according to one embodiment of the invention.

FIG. 8B depicts a schematic view of a containment system coupled to a sample system and a decontamination system according to one embodiment.

FIG. 8C depicts a schematic view of a plurality of valve assemblies coupled to a containment system, a sample system and a decontamination system according to one embodiment.

To facilitate understanding, identical reference numerals have been used, where possible, to designate identical elements that are common to the figures. It is contemplated that elements of one embodiment may be beneficially incorporated in other embodiments without further recitation.

DETAILED DESCRIPTION

Figure 1:
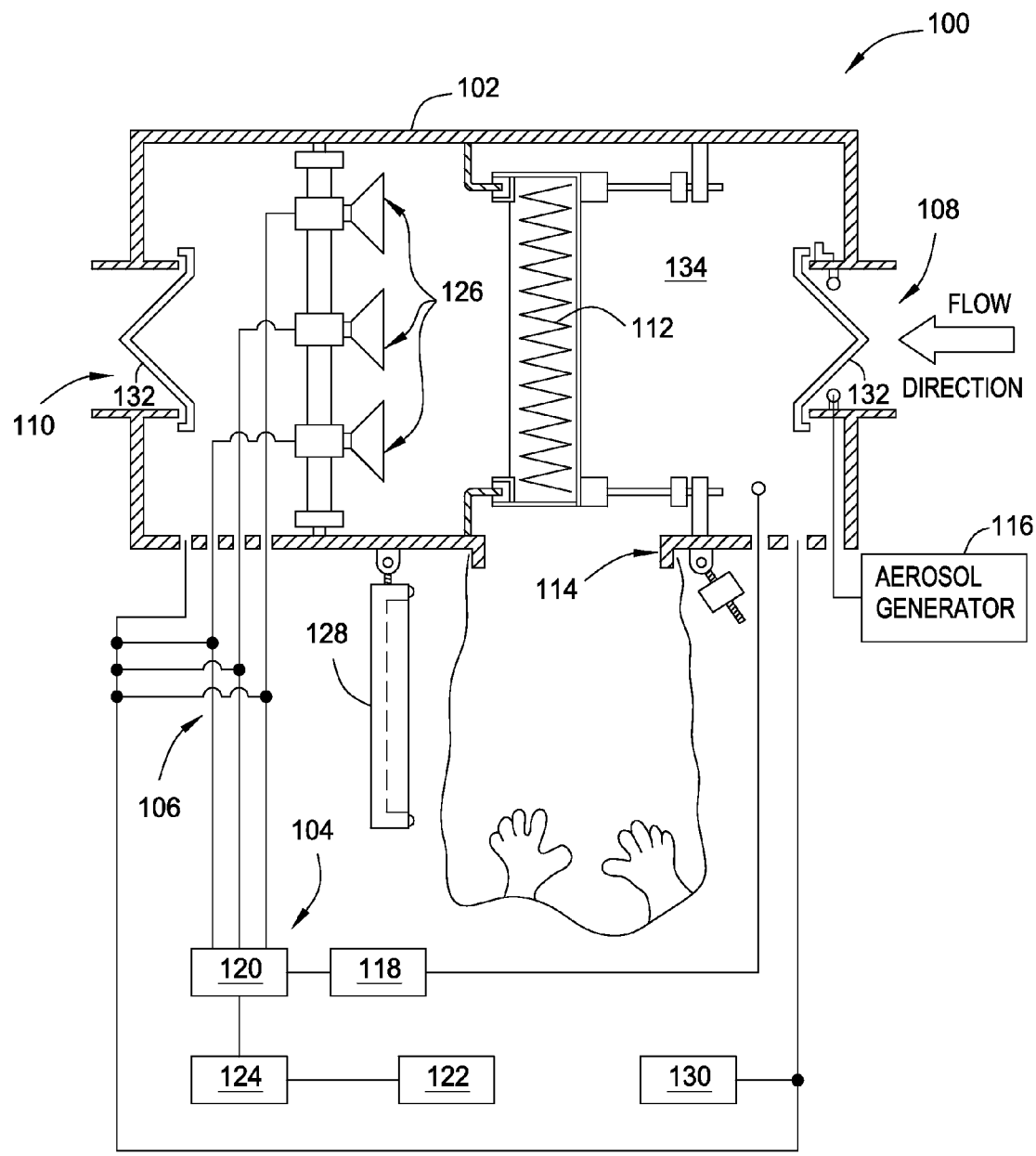
FIG. 1 depicts a simplified schematic diagram of an exemplary containment system coupled to a test system having a flow reverser according to one embodiment of the invention.

FIG. 1 depicts a simplified schematic diagram of an exemplary containment system 100 having a reversible flow test system 104 according to one embodiment of the invention. The reversible flow test system 104 is utilized to test a filter 112 disposed in the containment system 100. The reversible flow test system 104 is adapted to interface with a decontamination system 130. The decontamination system 130 is configured to provide a sterilization agent suitable for sterilizing the reversible flow test system 104. The terms sterilization agent and decontamination agent are used interchangeably herein to describe any vaporous, aerosol or gaseous element or compound used to clean, destroy or render harmless hazardous or viable materials or microorganisms or their spores that may be present in the test system 104 after testing the filter. In one embodiment, the sterilization or decontamination agent is an agent approved or recognized by the United States Center for Disease Control (CDC), the Food and Drug Administration (FDA), The National Science Foundation (NSF) or the Environmental Protection Agency (EPA).

The containment system 100 ensures that air exiting or being recycled in a facility is substantially free of hazardous particles. The containment system 100 includes a housing 102 having one or more filters 112 disposed therein. The containment housing 102 coupled to the reversible flow test system 104 by one or more tubes 106. One containment housing 102 that may be adapted to benefit from the invention is described in U.S. patent application Ser. No. 11/380,737, filed Apr. 28, 2006, which is incorporated by reference. Another containment housing 102 that may be adapted to benefit from the invention is a CAMCONTAIN™ Containment System, available from Camfil Farr, Inc., located in Washington, N.C. It is contemplated that other containment housings and other filter test equipment, including those available from other manufacturers, may be adapted to benefit from the invention. A more detailed description of a containment housing similar to the housing 102 is provided with reference to FIG. 7 below.

The containment housing 102 generally includes an inlet port 108 and an outlet port 110. The inlet port 108 receives air or other gases from a working environment of a facility, such as a biological safety lab, pharmaceutical manufacturing facility, biotechnology research lab, flow bench, or production facility, among others. The filter 112 disposed in the containment housing 102 is arranged such that air or other gases entering the containment housing 102 through the inlet port 108 must pass through and be filtered by the filter 112 prior to exiting the containment housing 102 through the outlet port 110. Dampers 132 may be utilized to control the rate of flow through the ports 108, 110 and/or to isolate an interior volume 134 of the containment housing 102 from upstream and/or downstream duct works. The containment housing 102 also includes a bag-in/bag-out filter replacement port 114 sealable by a door 128 for removing and replacing the filter 112 in the conventional manner.

The reversible flow test system 104 includes the test equipment necessary to test the filter 112 disposed within the housing 102, such as an aerosol generator 116, a diluter 118, a sampling system 120, a vacuum pump 122 and a flow reverser 124 coupled by tubing. The aerosol generator 116 supplies an aerosol challenge to the upstream side of the filter 112. The aerosol generator 116 provides the aerosol in a sufficient concentration to provide a statistically valid test of the filter 112.

The sampling system 120 includes a photometer, particle counter, or other equipment suitable for leak and/or efficiency testing of the filter 112. The sampling system 120 provides a metric indicative of the number of particles present in the air samples. The sampling system 120 obtains air samples from one or more probes 126 or ports positioned downstream of the filter 112 mounted in the housing 102. The probes 126 may be stationary or configured to scan the downstream face of the filter 112, as known in the art. The sampling system 120 also obtains samples from one or more ports positioned upstream of the filter 112 mounted in the housing 102. The diluter 118 is utilized to reduce the particle concentration of the sample obtained upstream of the filter 112 prior to entering the sampling system 120 as known in the art. The difference in the number of particulates in the samples taken from the upstream samples relative to the downstream samples may be utilized to determine filter efficiency and/or pin-hole leaks in the filter 112.

The vacuum pump 122 aides in circulation of the air sample and/or a sterilization agent from the decontamination system 130 through the sampling system 120. Any suitable pump may be used so long as the pump is compatible with the sterilization agent.

The vacuum pump 122 is coupled to the sampling system 120 and the decontamination system by the flow reverser 124. In one embodiment, the flow reverser 124 includes one or more valves, such as a spool valve or flow circuit comprised of appropriate shut-off valves and tees, arranged to switch selectively reverse the direction of the flow of the sterilization agent through the sampling system 120 by changing the state of the one or more valves comprising the flow reverser 124.

Figure 2A:
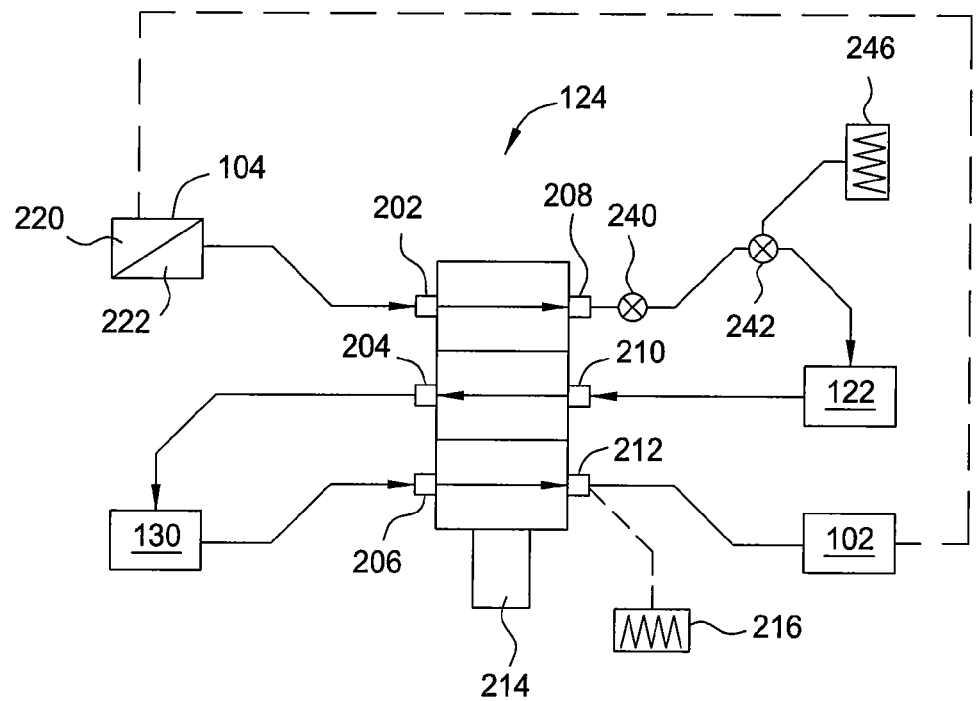
FIGS. 2A-B are schematic diagrams of one embodiment of a flow reverser in different operational states.
Figure 2B:
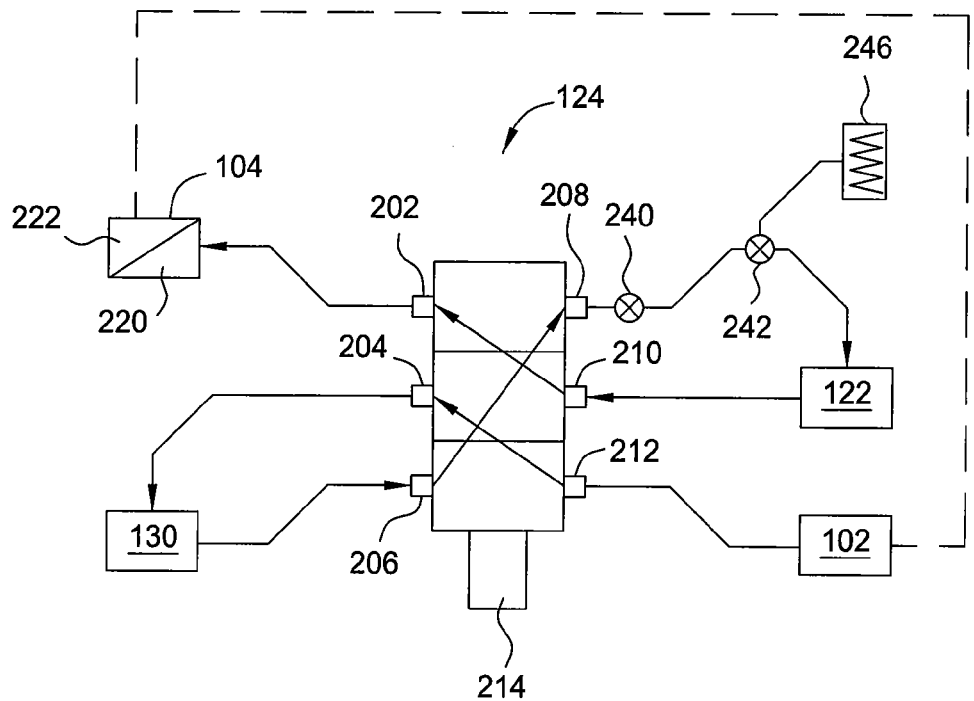

FIGS. 2A-B are schematic diagrams of one embodiment of the flow reverser 124 in different operational states. In the embodiment depicted in FIG. 2A, the flow reverser 124 is a spool valve that includes a first port 202 connected to the test system 104, a second port 204 connected to an inlet of the decontamination system 130, a third port 206 connected to an outlet of the decontamination system 130, a fourth port 208 connected to an inlet of the vacuum pump 122, a fifth port 210 connected to an outlet of the vacuum pump 122 and a sixth port 212 coupled to the housing 102. Alternatively, the sixth port 212 coupled to atmosphere through a HEPA filter 216 (shown in phantom) instead of being coupled to the housing 102.

Operational state of the flow reverser 124 is controlled by an actuator 214. In different operational states, different ports of the flow reverser 124 are respectively connected. The actuator 214 of the flow reverser 124 may be electric, pneumatic, hydraulic, manual or other type of actuator.

A first operational state of the flow reverser 124 is depicted in FIG. 2A. In the first operational state of the flow reverser 124, the first port 202 is coupled to the fourth port 208, the second port 204 is coupled to the fifth port 210 and the third port 206 is coupled to the sixth port 214. In the first operational state, the vacuum pulled by the vacuum pump 122 creates pressure gradient across the test system 104. The pressure gradient in the test system 104 includes a low pressure region 222 proximate the flow reverser 124 and a high pressure region 220 proximate the test system 104. As the relative humidity is proportional to pressure, the relative humidity within the test system 104 is highest in the high pressure region 220 proximate the housing 102 and lowest in the low pressure region 222 proximate the pump 122 and flow reverser 124.

A second operational state of the flow reverser 124 is depicted in FIG. 2B. In the second operational state of the flow reverser 124, the first port 202 is coupled to the fifth port 210, the second port 204 is coupled to the sixth port 214 and the third port 206 is coupled to the fourth port 208. In the second operational state, the vacuum pulled by the vacuum pump 122 pulls the sterilization agent produced by the decontamination system 130 through the vacuum pump 122 and pushes the sterilization agent into the test system 104, thereby creating a different pressure gradient across the test system 104. The pressure gradient in the test system 104 is now opposite of the pressure gradient present in the system 104 when the flow reverser 124 is in the first operational state, such that the pressure gradient in the test system 104 now has the low pressure region 222 proximate the housing 102 and the high pressure region 220 proximate the pump 122 and flow reverser 124. As the relative humidity is proportional to pressure, the relative humidity within the test system 104 is now highest proximate the vacuum pump 122.

It has been found that the effectiveness of the sterilization agent is greater in regions of the test system 104 having moderately high relative humidity. The presence of a moderately high relative humidity increases the concentration of the sterilization agent on the surfaces of the tubing of the test system 104 and other surfaces. The humidity of the sterilization agent in the test system 104 may be controlled to between about 60 to 80 percent relative humidity (RH), such as 65 to 75 percent RH, for good decontamination results. Thus, by changing the state of the flow reverser 124, the humidity gradient within the test system 104 is reversed to ensure that portions of the test system that have low pressure/humidity only during a portion of the decontamination cycle, and are exposed to higher pressure/humidity during other portions of the decontamination cycle. Thus, by decontaminating the test system 104 with the flow reverser 124 changed at least once between the first and second operations states, good humidity levels throughout the entire test system 104 are achieved to ensure effective sterilization with minimal soak times.

The flow reverser 124 or flow circuitry coupled thereto may also include a shut-off valve 240, a by-pass valve 242 and a HEPA filter 246. The shut-off valve 240 is disposed between the fourth outlet port 208 of the flow reverser 124 and the inlet of the vacuum pump 122. The shut-off valve 240 has a normally open state, but may be selectively closed to isolate the inlet of the vacuum pump 122 from the test system 104 during optional soak periods of the decontamination cycle (i.e., periods of no flow within the test system 120). With the shut-off valve 240 closed, the pressure gradient within the test system 104 begins to dissipate, and the pressure and humidity within the low pressure region 222 beings to rise while the pressure and humidity in the high pressure region 220 falls, thereby increasing the effectiveness in the regions having low pressure while the vacuum pump 122 is drawing from the test system 104. It has been found that the RH in the low pressure region 222 may increase up to 10% while the shut-off valve 240 is closed during a soak period.

The by-pass valve 242 is opened while the shut-off valve 240 is closed to couple the HEPA filter 246 to the inlet of the vacuum pump 122. The vacuum pump 122 may then draw air through the HEPA filter 246 while isolated from the test system 104 to avoid damage to the vacuum pump 122.

Figure 2C:
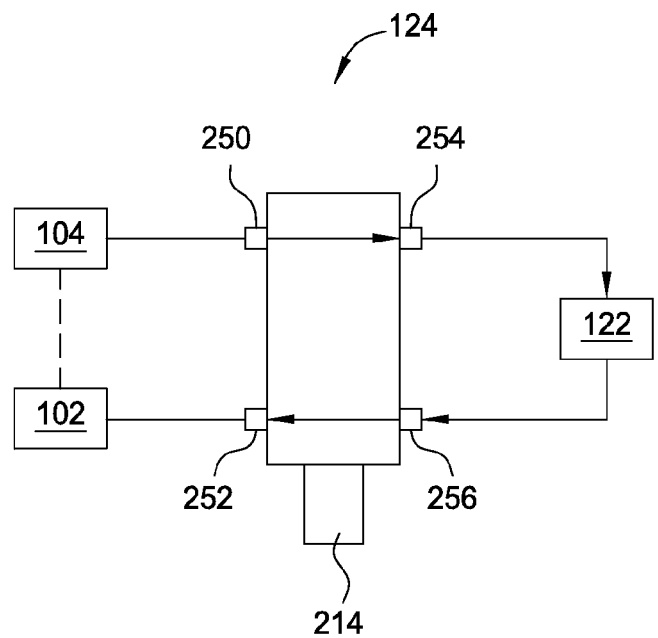
FIGS. 2C-D are schematic diagrams of another embodiment of a flow reverser in different operational states.
Figure 2D:
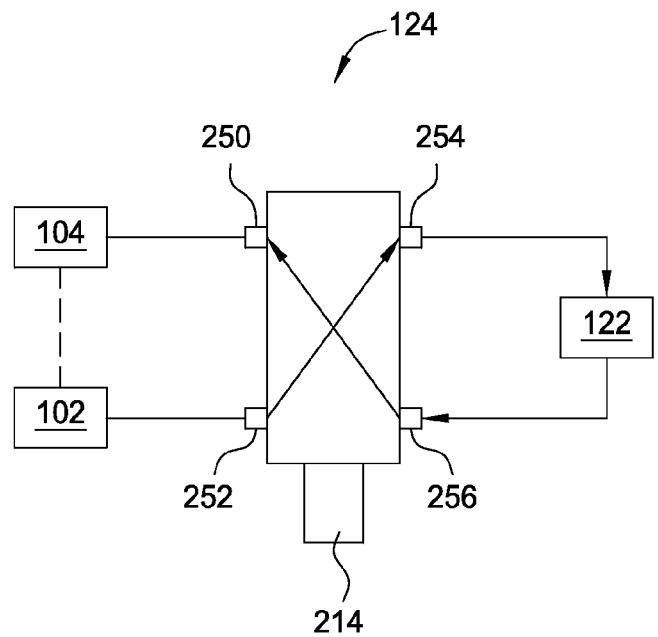

FIGS. 2C-D depict another embodiment of the flow reverser 124. In the embodiment depicted in FIG. 2C, the flow reverser 124 is a 4-way valve that includes a first port 252 connected to the test system 104, a second port 254 connected to the containment housing 102, a third port 256 connected to an inlet of the vacuum pump 122 and a fourth port 258 connected to an outlet of the vacuum pump 122. The flow reverser 124 may be operated by an actuator, such as the actuator 214, to change operational state of the flow reverser 124.

A first operational state of the flow reverser 124 is depicted in FIG. 2C. In the first operational state of the flow reverser 124, the first port 252 is coupled to the third port 256 and the second port 254 is coupled to the fourth port 258. In the first operational state, the vacuum pulled by the vacuum pump 122 creates pressure gradient across the test system 104 as discussed above.

A second operational state of the flow reverser 124 is depicted in FIG. 2D. In the second operational state of the flow reverser 124, the first port 252 is coupled to the fourth port 258 and the second port 254 is coupled to the third port 256. In the second operational state, the vacuum pulled by the vacuum pump 122 pulls air, which includes sterilization agent previously introduced to the containment housing 102, through the vacuum pump 122 and pushes the air and sterilization agent into the test system 104, thereby reversing the pressure gradient previously created in the test system 104 while the flow reverser 124 was in the first operational state. Since the pressure gradient in the test system 104 produced with the flow reverser 124 in the second operational state is the opposite of the pressure gradient produced when the flow reverser 124 is in the first operational state, the pressure gradient in the test system 104 now has a low pressure region proximate the test system 104 and a high pressure region proximate the flow reverser 124 and pump 122. Thus, reversing of the pressure gradient allow high concentrations of the sterilization agent to be present during at least a portion of the decontamination cycle in every region of the tubing and other equipment comprising test system 104.

Figure 3:
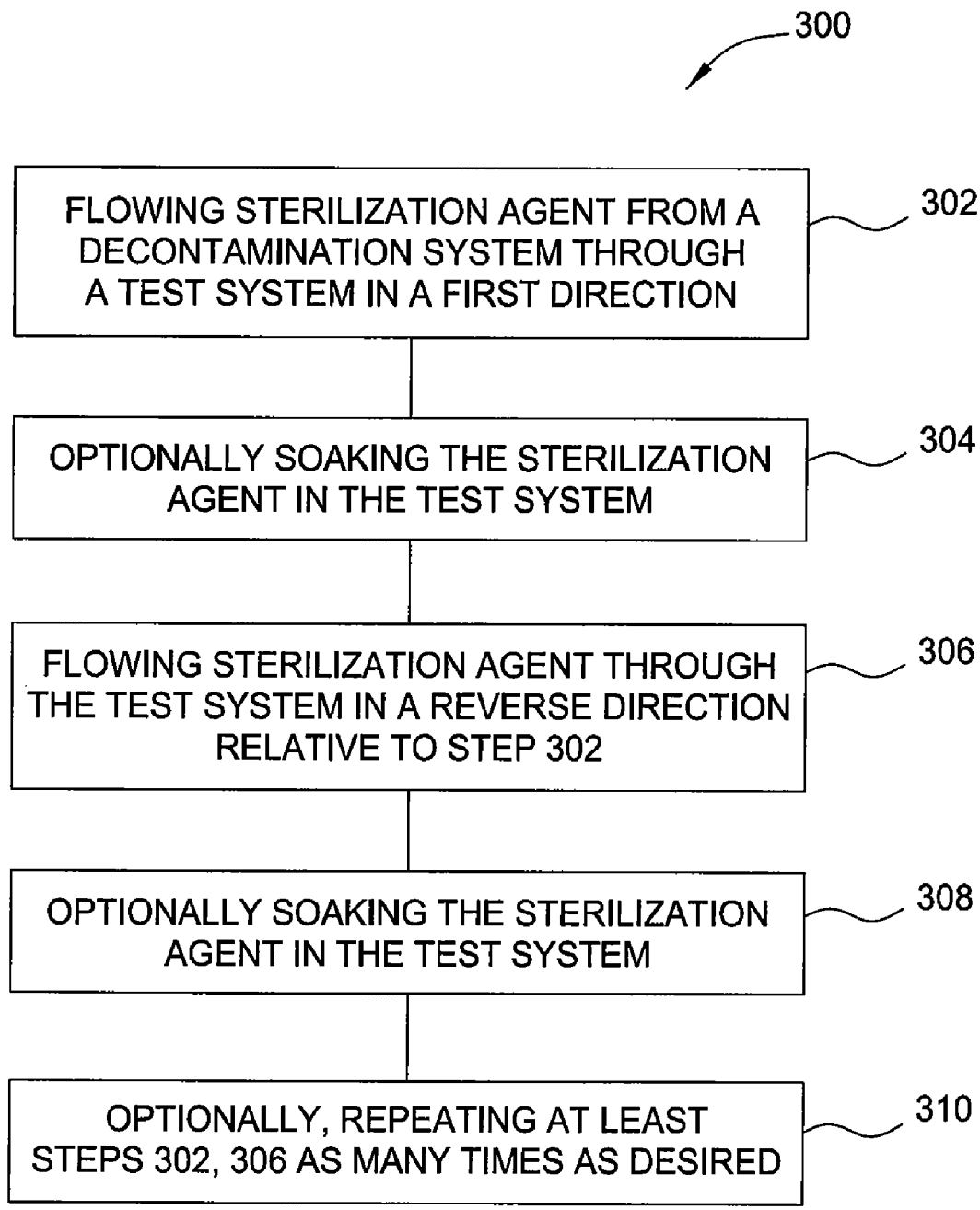
FIG. 3 is a flow diagram of one embodiment of a method for decontaminating tubing.

FIG. 3 is a flow diagram of one embodiment of a method 300 for decontaminating tubing, such as tubing 106 coupling the test system 104 to the contamination housing 102 and/or tubing within the test system 104 itself. In one embodiment, the method 300 begins by flowing a sterilization agent from the decontamination system 130 through the tubing of test system 104 in a first direction at step 302. If the system consists of multiple loops or circuits controlled by valves, these circuits may be charged simultaneously or sequentially by operating the valves accordingly. During step 302, the flow reverser 124 is in the first operational state. The duration of step 302 may be from about 1 second to about 5 minutes, depending on the volume of the circuit. An acceptable cycle involving multiple circuits might include sequential charging of each circuit for 5 to 30 seconds and a forward flow direction time of 10 seconds to 10 minutes depending upon the exact configuration of the system. In other systems, the flow direction may be reversed by reversing the direction of the vacuum pump 122.

At an optional soak step 304, the shut-off valve 240 may be closed and the by-pass valve 242 may be opened to allow the sterilization agent in the test system 104 to soak (i.e., be in a substantially non-flow condition). Soaking allows the sterilization agent to disperse with the test system 104 while allowing for pressure to rise in areas of low pressure generated during step 302, such as the region of the test system 104 proximate the vacuum pump 122. The duration of the soak step 304 may be from about 10 seconds to about 10 minutes, such as about 1 minute to about 6 minutes. It is contemplated that the soak step 304 may be performed without use of the shut-off valve 240 and the by-pass valve 242 by turning off the vacuum pump 122, and optionally, changing the state of the flow reverser 124.

At step 306, the flow of the sterilization agent through the tubing 106 of test system 104 is reversed. The flow of the sterilization agent through the tubing 106 of test system 104 may be reversed by changing the operational state of the flow reverser 124 to the second operational state. The duration of the soak step 304 may be from about 10 seconds to about 10 minutes, such as about 1 minute to about 6 minutes.

Figure 4:
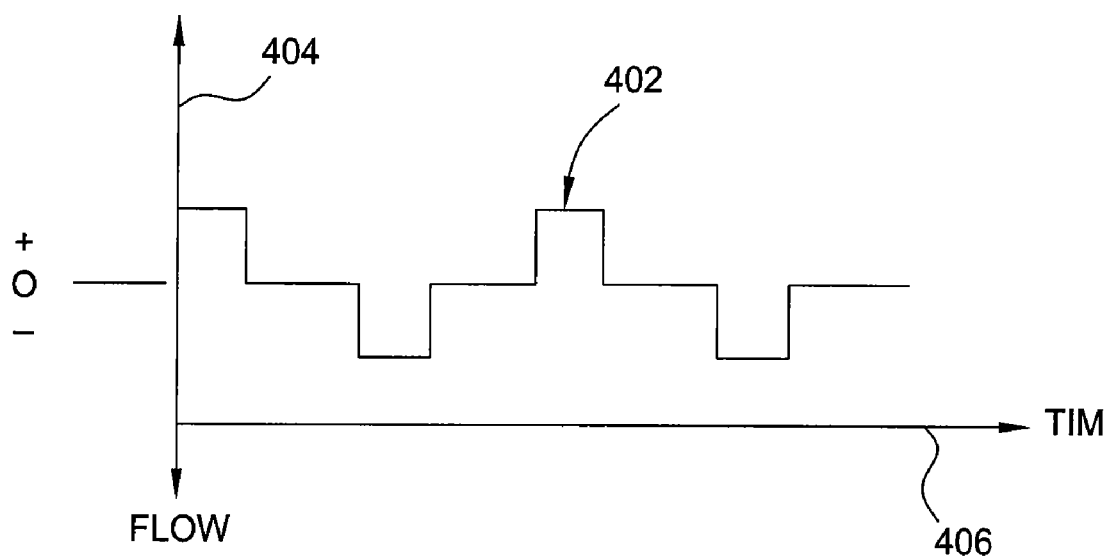
FIG. 4 is a chart depicting a sequence of flow direction through tubing during one embodiment of a method for decontaminating tubing.

At an optional soak step 308, the shut-off valve 240 may be closed and the by-pass valve 242 may be opened to allow the sterilization agent in the test system 104 to soak after step 306. The soak step 308 may be shorter than the soak step 304. It is contemplated that the soak step 308 may be performed without use of the shut-off valve 240 and the by-pass valve 242 by turning off the vacuum pump 122, and optionally, changing the state of the flow reverser 124. The duration of step 308 may be from about 10 seconds to about 10 minutes, such as about 1 minute to about 6 minutes. At an optional step 310, the sequence of steps 302, 306 may be repeated as many times as desired. One or more of the optional soak steps 304, 308 may also be repeated at step 310. It is contemplated that the sterilization agent may be any sterilization agent suitable to decontaminate surfaces of hazardous particles from containment systems including, but not limited to formaldehyde ($CH_2O$) and chlorine dioxide ($ClO_2$), Hydrogen Peroxide ($H_2O_2$) among others. The target concentration of the sterilization agent and the duration of the decontamination cycle are a function of the sterilization agent used, the hazardous particles in the system, and other factors that may be specific to a particular application. The above example is provided utilizing Chlorine Dioxide as a sterilization agent, and a test system having an enclosed volume of approximately 5 cubic feet comprised of approximately 300 feet of 0.25 inch inside diameter tubing, 20 feet of 0.75 inch inside diameter tubing and other system components including filters, junction box (es), humidifier(s) and valves that contribute to total system volume. FIG. 4 is a graph 400 illustrating the flow changes within the test system 104 during one embodiment of the method 300. The graph 400 includes a flow trace 402 with flow on the vertical axis 404 and time on the horizontal axis 406. In the embodiment of the method 300 depicted in the graph 400, optional soak steps 304 and 308 are included. Flow in the first direction though the test system 104 is illustrated as a positive value on the vertical axis 404 while flow in the opposite direction (e.g., second direction) is illustrated as a negative value on the vertical axis 404.

Figure 5:
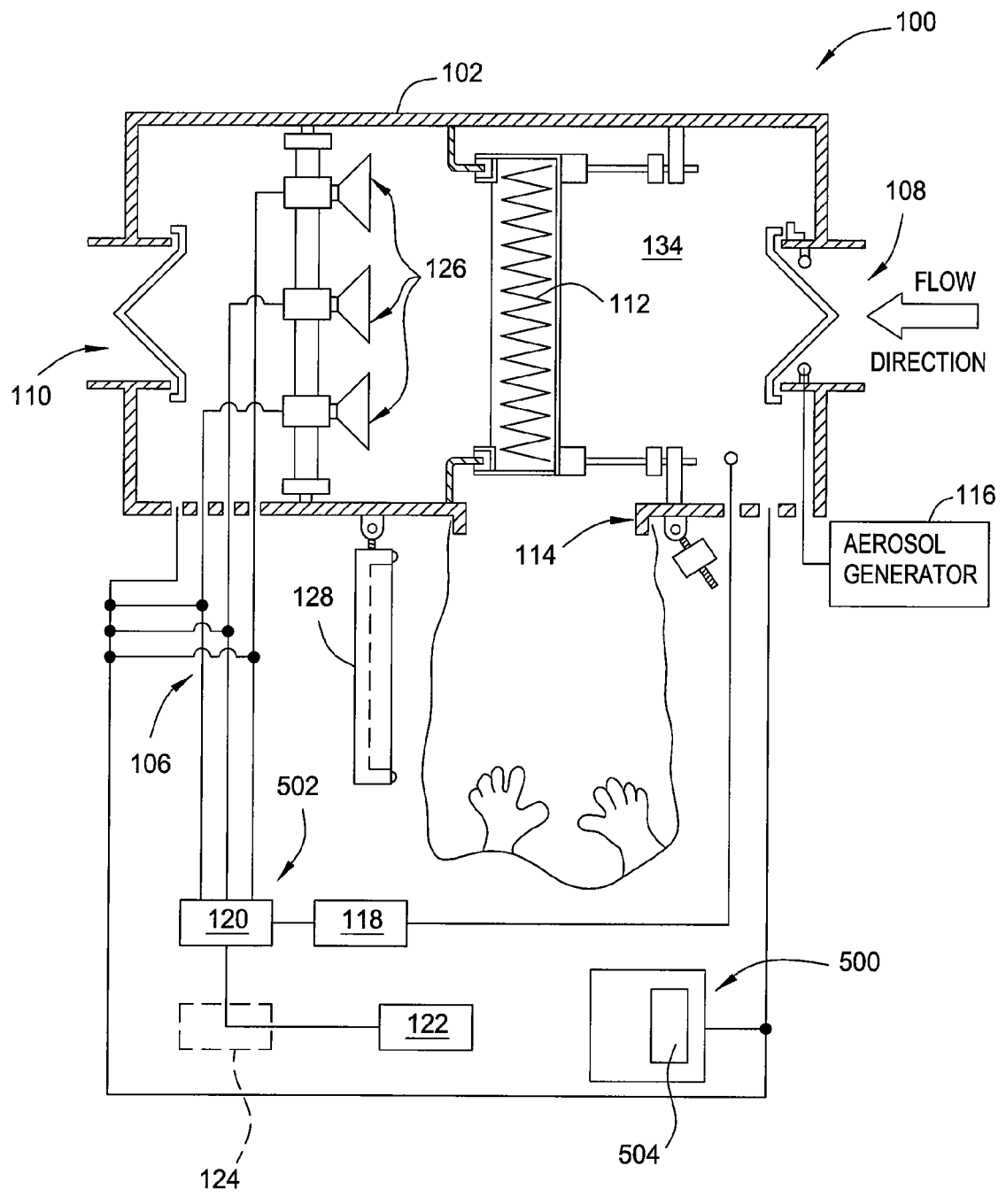

FIG. 5 is depicts a simplified schematic diagram of one embodiment of a decontamination system 500 that may be utilized with a containment system 100 having a test system 502. The test system 502 is substantially identical to the reversible flow test system 104 described above, except for that the flow reverser 124 is optional. The decontamination system 500 incorporates a humidifier 504 to provide better control of the humidity in the test system 502 during sterilization, and as such, provides increased effectiveness of the decontamination process. The humidifier may be of various designs including thermal, ultrasonic or aerosol nozzle types.

Figure 6:
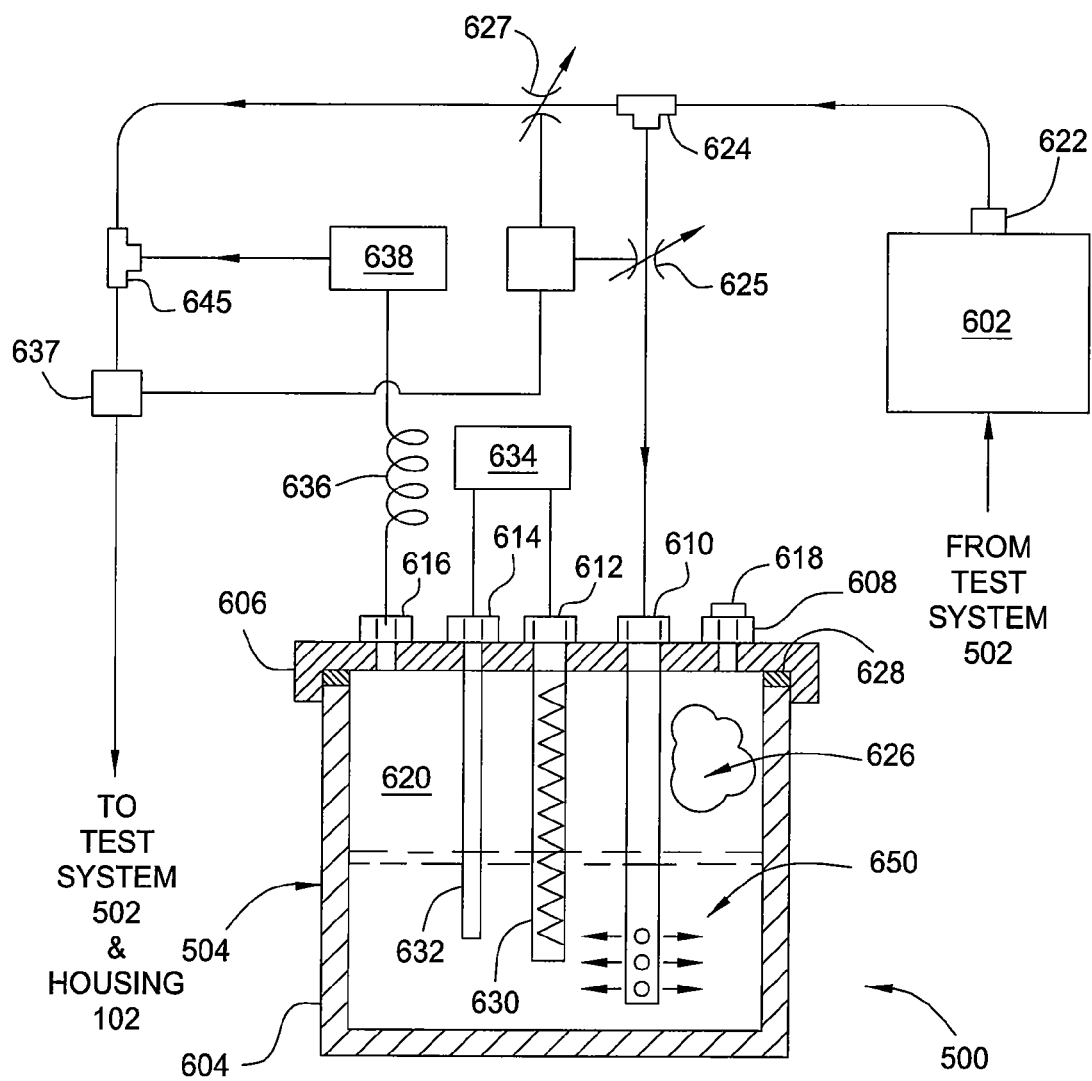
FIG. 6 depict one embodiment of a decontamination system.

Referring additionally to FIG. 6, the decontamination system 500 includes a sterilization agent generator 602 coupled to the humidifier 504. The sterilization agent generator 602 may be any suitable sterilization agent generator now known or developed in the future.

The humidifier 504 includes a canister 604 sealed by a lid 606. In one embodiment, a gasket 628 is disposed between the canister 604 and the lid 606 to provide a seal therebetween. At least one of the canister 604 or the lid 606 includes a fill port 608, an inlet port 610, a heater port 612, a thermocouple port 614 and an outlet port 616. The fill port 608 may be sealed by a cap or plug 618, which may be removed to allow an interior volume 620 of the canister 604 to be filled with a fluid 650, such as water, to an appropriate level for humidity generation. The inlet port 610 is coupled to an output port 622 of the sterilization agent generator 602 by a tee 624. A bubbler 626 is disposed in the interior volume 620 of the humidifier 504 and coupled to the inlet port 610. The bubbler 626 allows the sterilization agent to be bubbled up through the fluid disposed in the humidifier 504 to generate a mixture of sterilization agent and water vapor within the interior volume 620.

A resistive heater 630 is provided to heat the fluid and/or water vapor in the humidifier 504. The resistive heater 630 may be disposed on the exterior of the canister 604 or in the interior volume 620 of the humidifier 504 as shown in FIG. 6. A thermocouple 632 is disposed in the humidifier 504 to provide a metric indicative of the temperature of the fluid and/or water vapor in the humidifier 504. The resistive heater 630 and thermocouple 632 are coupled through the heat and thermocouple ports 612, 614 to a controller 634 to provide control of the temperature of the fluid and/or water vapor in the humidifier 504.

The mixture of sterilization agent and water vapor generated within the interior volume 620 of the canister 604 exits the humidifier 504 through the outlet port 614. A cooling coil 636 and steam trap 638 are coupled to the outlet port 614 to minimize the amount of liquid entrained in the mixture leaving the humidifier 504. The mixture of sterilization agent and water vapor is mixed in with the sterilization agent from the sterilization agent generator 602 at a tee 640, which couples the combined flows to the test system 502.

The decontamination system 500 having the humidifier 504 coupled in parallel to the output of the sterilization agent generator 602 has illustrated a beneficial increase in humidity levels in the test system 502 during decontamination over conventional designs. The decontamination system 500 has been able to maintain the humidity within the test system 502 in the range of 60 to 80% RH, which provides more efficient sterilization of the tubing utilized in the test system 502. As discussed above, the decontamination system 500 may be utilized in the tube sterilization method 300 described above, or in other decontamination processes. It is also anticipated that in another embodiment, the humidifier described above can be fitted with a port allowing the introduction of reagents to generate the decontamination agent, thereby allowing the humidifier to also act as a decontamination agent generator as well.

Figure 7:
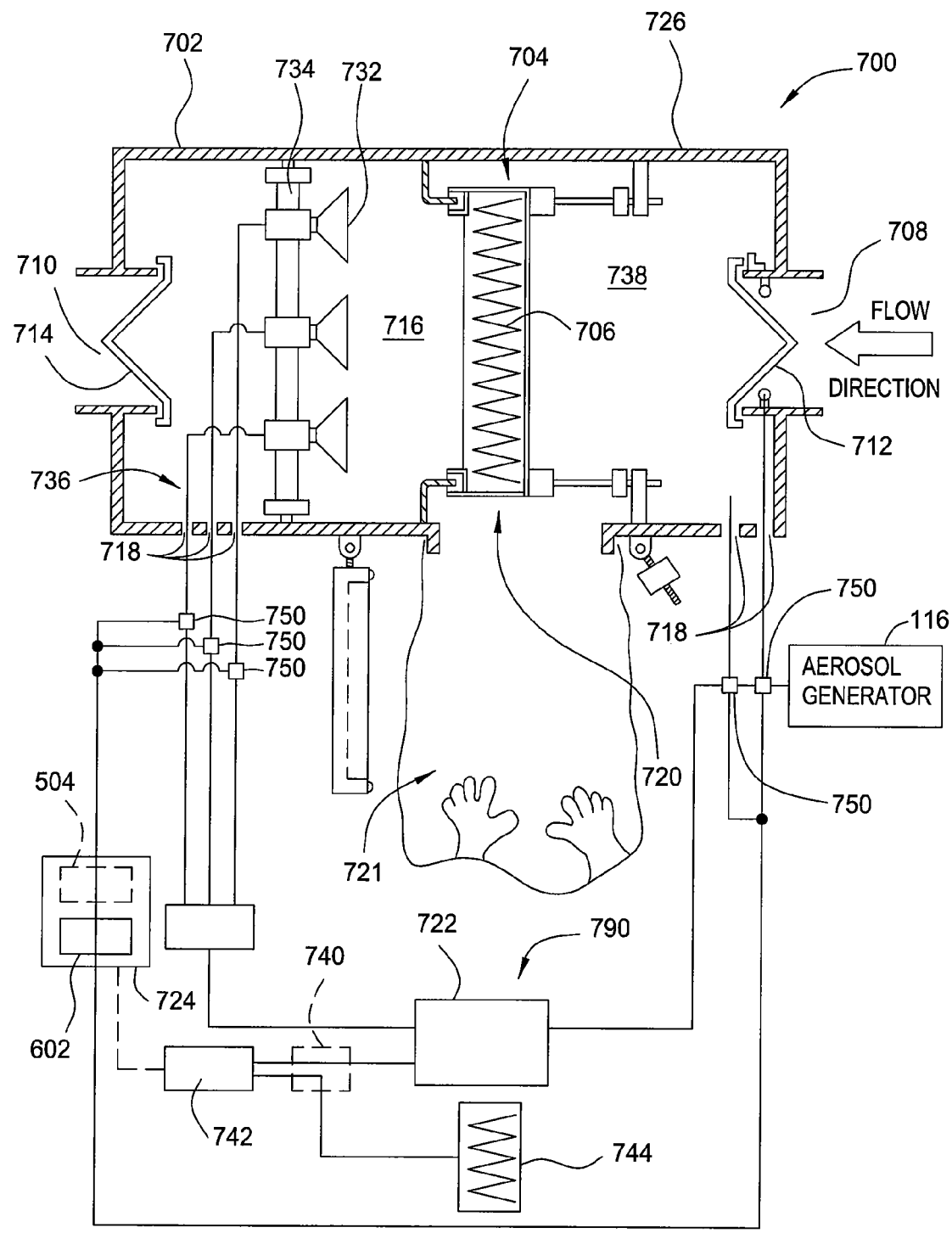
FIG. 7 depicts a simplified schematic diagram of another embodiment of a containment system according to one embodiment of the invention.

FIG. 7 is a sectional schematic view of another embodiment of a containment system 700. The containment system 700 ensures that air exiting or being recycled in a facility is substantially free of hazardous matter. The containment system 700 is similar to the housings described above and generally includes a housing 702 having one or more filters 706 disposed therein.

In one embodiment, the housing 702 includes a filter mounting portion 704 for sealingly mounting the filter 706 to the housing, an airflow inlet aperture 708 and an airflow exit aperture 710. Each aperture 708, 710 has a damper 712, 714 for controlling the flow of air through the housing 702 and filter 706. In one embodiment, the dampers 712, 714 may be configured with a bubble-tight seal so that leakage may be prevented through the apertures 708, 710.

The housing 702 includes a sealable filter access port 720 formed through the housing 702 adjacent the filter mounting portion 704 to facilitate installation and replacement of the filter 706. As common practice, the sealable filter access port 720 includes a bag-in bag-out system 721 to prevent exposure of technicians to hazards during filter replacement.

The housing 702 also includes a test section 716 and a plenum section 738. The test section 716 is positioned downstream of the filter mounting portion 704 while the plenum section 738 is positioned upstream of the filter mounting portion 704. The test section 716 includes one or more downstream sample ports utilized to test the filter 706 disposed in the housing 702. The plenum section 738 is generally configured to provide sufficient space for mixing elements to provide an even distribution of aerosol challenge upstream of the filter 706.

A plurality of sample ports 718 are formed through the housing 702 to accommodate taking samples from the test section 716 and delivering aerosol to the plenum section 738. Each port 718 is fitted with a valve assembly 750. The valve assembly 750 is selectable between at least three states. In a first state, the valve assembly 750 prevents flow through the port 718. In a second state, the valve assembly 750 fluidly couples the port 718 to a test system 790 that includes the test equipment necessary to test the filter 706 disposed within the housing 702, such as an aerosol generator, dilutor and sampling system 722. In a third state, the valve assembly 750 seals the port 718 but fluidly couples the test system 790 to a decontamination system 724.

The decontamination system 724 generally provides an agent suitable for neutralizing hazardous agents that may be present in the test system 790 after testing the filter 706. The decontamination system 724 may additionally be utilized to decontaminate the housing 702 prior to filter testing or as desired. The decontamination system 724 may optionally be configured similar to the decontamination system 500 described above to include a humidifier 504 that raises the humidity of the sterilization agent being provided to the contamination housing 702 and test system 790 in the ranges discussed above. The valve assembly 750 will be described in greater detail below.

In the embodiment depicted in FIG. 7, the downstream sample ports 718 disposed in the test section 716 comprises one or more probes 732 and a support structure 734. The support structure 734 couples the one or more probes 732 to the housing 702. The support structure 734 may statically hold the probes in a predefined position, or may be configured with one or more actuators, such as an x/y displacement mechanism, which dynamically positions (e.g., scans) the probe 732 along the downstream surface of the filter 706. The one or more probes 732 may have a design suitable for scan and/or efficiency testing. In one embodiment, the one or more probes 732 conform to IEST-RP-CC034 Recommended Practices.

The valve assembly 750 can be a single valve or a plurality of valves. The valve assembly 750 can have mechanical or automated actuation. The valve assembly 750 can include a manual or electronic lockout. The lockout prevents inadvertent actuation of the valve assembly 750. Further, the valve assembly 750 can have position sensors 752 (shown schematically) that provide the controller with a metric indicative of the state of the valve. The controller, in response to a metric, can electronically lockout the valve assembly 750 to prevent change in state of the valve assembly 750 so that the routing of gas flow through the valve assembly 750 cannot be changed. Further, the valve assembly 750 can have a sensor 754 (shown schematically) to determine if lines to the sample system 722 and/or decontamination system 724 are coupled to valve assembly 750 to prevent inadvertent actuation.

Figure 8A:
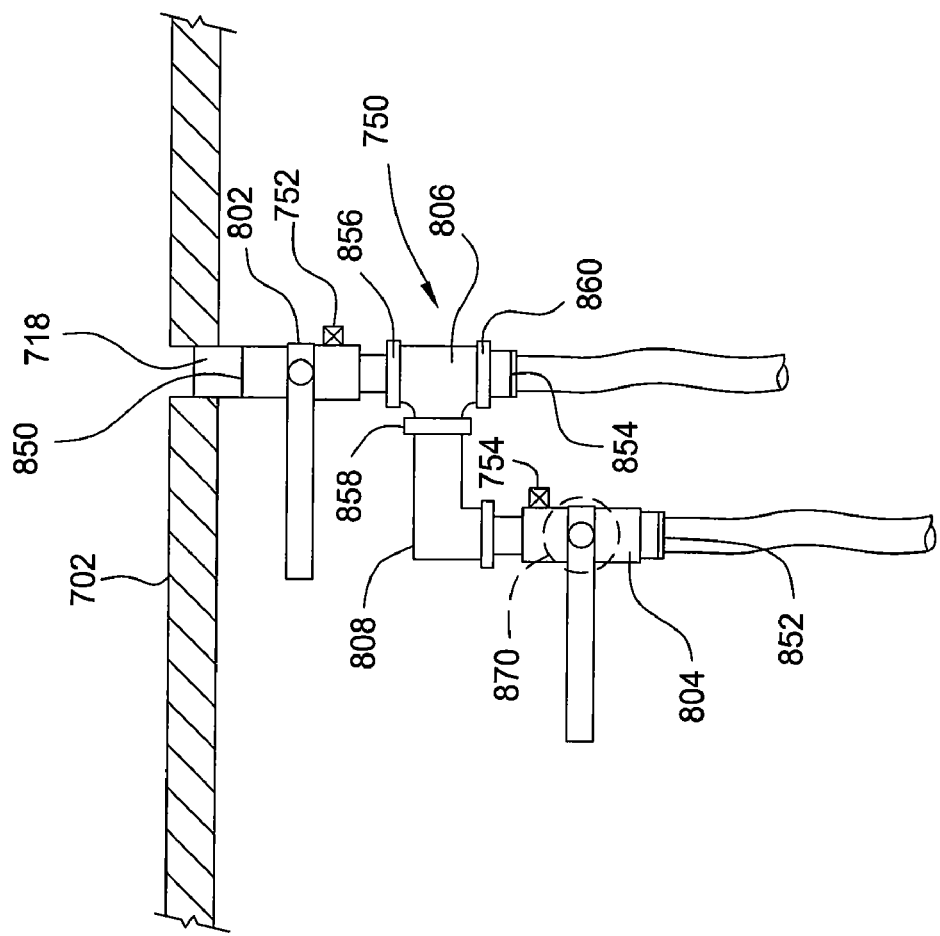
FIG. 8A depicts a view of one valve assembly according to one embodiment.

A valve assembly 750 is respectively coupled to a corresponding sample port 718, as shown in FIG. 8A-2C. The one or more valve assemblies 750 allow an operator to selectively control the flow between the test section 716, plenum section 738, the sample system 722 of the test system 790, and the decontamination system 724. In one embodiment, each of the one or more valve assemblies 750 includes an isolation valve 802 and a decontamination valve 804. The valve assembly 750 alternatively may also be a single selector valve configured to seal the sample port 718, allow flow between the test section 716 and the sample system 722, the test section 716 and the decontamination system 724, or the decontamination system 724 and the sample system 722. The valve assemblies 750 can each comprise a first port 850, a second port 852 and a third port 854. The first port 850 fluidly couples the valve assembly 750 to the sample port 718. The second port 852 fluidly couples valve assembly 750 to the decontamination system 724. The third port 854 fluidly couples the valve assembly 750 to the sample system 722.

FIG. 8A depicts one embodiment of the valve assembly 750. The valve assembly 750 comprises an isolation valve 802 and a decontamination valve 804 configured to control flow between the test section, the sample system 722 and the decontamination system 724. The upstream of the isolation valve 802 is coupled to the port of the housing 702. The downstream side of the isolation valve 802 is coupled to a tee fitting 806 at a first tee port 856. The second side of the tee fitting 806 is coupled to the decontamination system 724 through the decontamination valve 804 at a second tee port 858. The third side of the tee fitting 806 is coupled to the sample system 722, at a third tee port 860.

The isolation valve 802 is in fluid communication with the corresponding sample port 718. The isolation valve 802 selectively isolates the sample system 722 from the test section 716 or the plenum section 738. As shown in FIGS. 8A-2C, the isolation valve 802 is in the closed position. In the closed position, the isolation valve 802 prevents fluid flow from exiting the test section 716 through the sample port 718.

The decontamination valve 804 is in fluid communication with the sample system 722. The decontamination valve 804 selectively isolates the decontamination system 724 from the tee fitting 806. As shown in FIGS. 8A-2C, the decontamination valves 804 are in the closed position. In the closed position, the decontamination valve 804 prevents fluid flow from the decontamination system 724 to the sample system 722.

In one embodiment, the isolation valve 802 and the decontamination valve 804, as shown in FIG. 8A-2C, are both hand operated ball valves. However, it is contemplated that any valve capable of selectively controlling and isolating flow may be used including, but not limited to, a single selector valve, a gate valve, a spool valve, a pneumatic valve, a solenoid valve, a control valve or other suitable flow control device. Although the valve assembly 750 is shown as being hand operated, it is contemplated that the valve assembly 750 may be automatically actuated to change the state of the valve. Thus, the operation of one or both of the isolation valve 802 and the decontamination valve 804 may be automatically controlled from a controller 836. For example, the valve and/or valves comprising one or more of the valve assemblies 750 may include an automatic actuator 870 (shown in phantom). The automatic actuator 870 may be a servo motor, a stepper motor, a rotary actuator, a pneumatic or hydraulic actuator, a linear actuator, solenoid or other actuator suitable for changing the state of the valve in response to a signal from the controller 836.

The valve assembly 750 may also include the sensor 752 and/or 754 that provides the controller 836 with a signal indicative of the position (i.e., flow state) and/or if the valve is connected to a conduit (so that fluids can not inadvertently exit the valve into surrounding environment), thus enabling a lockout if the valves are not properly sequenced or are in an unintended state. The lockout may be mechanical, or electronic. The sensors 752, 754 may be a flow sensor interfaced with the fluid conduits of the valve assembly, a proximate indicator configured to detect if the valve assembly 750 is coupled to appropriate conduits, or an encoder, limit switch or other sensor suitable for detecting the open and/or closed state of the one or more valves comprising the valve assembly 750.

In an alternative embodiment, one or both of the isolation valve 802 and the decontamination valve 804 may include a one-way (check) valve. The one-way valve associated with the isolation valve 802 may be arranged to allow fluid flow from the test section 716 to the sample system 722 while preventing flow in the opposite direction. The one-way valve associated with the decontamination valve 804 may be arranged to allow fluid flow from the decontamination system 724 to the sample system 722 while preventing flow in the opposite direction.

FIG. 8B depicts the containment system 700 coupled to the test system 790, an aerosol generator 822 and the decontamination 724 system to facilitate in-situ testing of the filter 706 disposed in the housing 702. The decontamination system 724 selectively decontaminates the test system 790, the aerosol generator 822, and/or the dilutor 824. The decontamination valves 804 may be selectively opened to allow a decontamination agent to enter the sample system 722 of the test system 790. The isolation valve 802 is generally closed while the decontamination valve 804 is open. The isolation valves 802 selectively prevent the agents from the decontamination system 724 from entering the interior of the housing 702 through the sample ports 718. The decontamination system 724 circulates a sterilization (decontamination) agent through any of the systems to be decontaminated. As shown, the decontamination system 724 couples to the decontamination valves 804 via one or more decontamination lines 835. The decontamination lines 835 couple directly to the decontamination valves 804 or to an intermediate coupler, such as a decontamination manifold 813, between the decontamination valves 804 and the decontamination lines 835. The intermediate coupler may be any device for sealingly coupling the decontamination system 724 to the decontamination valve 804. For example, the intermediate coupler may be a quick connect. The intermediate coupler allows an operator to quickly couple the decontamination lines 835 to the decontamination valves 804.

The aerosol generator 822 supplies an aerosol challenge to the upstream side of the filter 706 through at least one of the valve assemblies 750 coupled to the plenum section 738. The aerosol generator 822 provides an aerosol to the plenum section 738 of sufficient concentration to provide a statistically valid test of the filter 706. The aerosol generator 822 may be coupled to the sample manifold 820 through a decontamination return valve 807.

The test system 790 measures the particles present in the air samples taken from the test section 716 and plenum section 738 of the containment system 700 through the sample ports 718 of that leak or efficiency determinations may be make. The test system 790 includes a sample system 722, a dilutor 824, one or more lines 814, and an exhaust filter 744. The one or more lines 814 (i.e., tubing) convey the air samples to the filter test equipment of the sample system 722. The filter test equipment may be a photometer, particle counter, or other equipment suitable for leak and/or efficiency testing of the filter 706. The filter test equipment provides a metric indicative of the number of particles present in the air samples. The measured air sample exiting the filter test equipment is exhausted from the sample system 722 through the exhaust filter 744. In embodiments wherein the vacuum pump 742 is directly coupled to the decontamination system 724, the filter 744 may be omitted.

The dilutor 824 is also coupled to the upstream side of the filter 706 through at least one of the valve assemblies 750 coupled to the plenum section 738. The dilutor 824 is provided a sample of the air and aerosol present in the plenum section 738 through the valve assembly 750 when the isolation valve 802 is open and the decontamination valve 804 is closed. The dilutor 824 is configured to dilute the upstream sample a predefined amount so that the concentration of particles provided to the filter test equipment of the sample system 722 is within the operational limits of the filter test equipment so that an upstream concentration limit may be calculated for use in determining the filtration efficiency and/or leak threshold.

The one or more lines 814 coupling the one or more valve assemblies 750 to the filter test equipment of the sample system 722 may each be coupled to a solenoid valve 818 so that samples from each line may be sequenced through the filter test equipment. The solenoid valves 818 may be independently operated and controlled. In one embodiment, each solenoid valve 818 controls the flow from each line 814 into a sample manifold 820. The common outlet of the sample manifold 820 is fluidly coupled to the filter test equipment of the sample system 722. In this embodiment, any one, or combination, of the solenoid valves 818 may open in order to test the air sample from that particular probe 732 (or dilutor 824) associated with the corresponding valve assembly 750.

A decay bypass valve 805 may be coupled to the upstream side of the filter 706 through at least one of the valve assemblies 750 coupled to the plenum section 738. In one embodiment, the decay bypass valve 805 couples the inlet of the dilutor 824 to the outlet of the filter test equipment of the sample system 722. In this embodiment, the decay bypass valve 805 may open in order to allow more rapid evacuation of the housing and system when performing vacuum pressure decay tests.

In one embodiment, the air leaving the filter test equipment of the sample system 722 passes through an exhaust filter 744. The exhaust filter 744 prevents hazardous particles which may be within the sample system 722 from being passed to the environment after sampling. The exhaust filter 744 may be any suitable filter.

The sample system 722 may optionally include a vacuum pump 742. The vacuum pump 742 aides in circulation of the air sample and/or a sterilization agent from the decontamination system 724 through the sample system 722. Any suitable pump or compressor may be used so long as the pump or compressor is compatible the sterilization agent.

Optionally, a flow reverser 740 (shown in phantom) may be disposed between the sample system 722 and the vacuum pump 742. The flow reverser 740 is similar to the flow reversers described above, and operates to reverse the flow direction of sterilization agent within the test system 722, for example, to enable performance of the method 300 described above with reference to FIG. 3. In another embodiment, the vacuum pump 742 may be a reversible pump that enables reversing the flow direction of sterilization agent within the test system 722 without the need of a flow reverser 740.

A bypass filter 832 may be coupled to the sample manifold 820. The bypass filter 832 may be any suitable filter, for example a HEPA filter. Air flow from the bypass filter 832 to the sample manifold 820 can be selectively controlled by a bypass valve 834. As shown, the bypass valve 834 is a solenoid valve, but may be any suitable valve. The bypass filter 832 provides air to the filter test equipment of the sample system 722 when the solenoid valves 818 interfaced with the one or more lines 814 are closed. The bypass filter 832 allows the pump of the filter test equipment of the sample system 722 to continue to circulate air. This prevents the pump or compressor from failing, thereby extending the service life of the filter test equipment of the sample system 722.

Referring primarily to FIG. 8B, the controller 836 includes control lines 838 for communicating with the various components of the sample system 722, the decontamination system 724, the valve assemblies 800, the solenoid valves 818, 830 and/or 834, the dilutor 824, and/or the aerosol generator 822. The controller 836 sends and receives data via the control lines 838. Optionally, the controller 836 may communicate using fluid, pneumatic, and/or wireless (e.g., infrared, RF, Bluetooth, etc.) signals with components described herein. The controller 836 may be configured to operate and monitor each of the respective components in an automated fashion (e.g., according to a preprogrammed sequence stored in memory) or according to explicit user input.

Although not shown, the controller 836 may be equipped with a programmable central processing unit, a memory, a mass storage device, and well-known support circuits such as power supplies, clocks, cache, input/output circuits, and the like. Once enabled, an operator may control the operation of the containment system 700, the sample system 722, the decontamination system 724, the aerosol generator 822 and the dilutor 824 by inputting commands into the controller 836. To this end, another embodiment of the controller 836 includes a control panel, not shown. The control panel may include a key pad, switches, knobs, a touch pad, etc. The controller 836 may further comprise a visual display.

During normal operation of the containment system 700 the valve assemblies 750 are in the first state. In the first state, the valve assemblies 750 prevent flow through the ports 718. In one embodiment, the isolation valve 802 is closed in the first state. The first state allows the containment system 700 to filter facility air through the housing 702 without contaminating the sample system 722. The valve assembly 750 remains in the first state until a filter test and/or certification is desired. When the filter test is desired, the sample system 722 is coupled to the valve assemblies 750.

To test the filter 706, the valve assemblies 750 are placed in the second state. In the second state, the valve assemblies 750 fluidly couple the ports 718 to the filter test equipment of the sample system 722 of the sample system 722 that are necessary to test the filter 706 disposed within the housing 702. In one embodiment, the second state is achieved by opening the isolation valve 802 while the decontamination valve 804 remains closed.

An aerosol challenge is provided by the aerosol generator to the plenum section of the housing 702 through the appropriate valve assembly 750. After the upstream challenge concentration has stabilized within the housing, the appropriate solenoid valve 818 is opened to allow the dilutor 824 to provide a sample to the filter test equipment of the sample system 722 so that the upstream concentration and/or leak threshold may be established. The appropriate solenoid valves 818 are actuated to provide downstream samples obtained through the probes 732 to the filter test equipment of the sample system 722. From the downstream samples, the filter efficiency and/or location of a leak may be determined. The pump or compressor of the filter test equipment of the sample system 722 can pull the air sample from the test section 716. The air sample travels via the one or more tubes 736 through the wall of the housing 702 and through the one or more valve assemblies 750. The air sample travels past the valve assemblies 750 and into the one or more lines 814 of the sample system 722. The decontamination system 724 remains isolated from the sample system 722. This prevents the flow of the air sample into the decontamination system 724 while causing the air sample to enter the sample system 722.

The air sample travels to the filter test equipment of the sample system 722 for testing. The filter test equipment of the sample system 722 tests the air sample. The filter test equipment of the sample system 722 can directly store and/or convey the information from the test to an operator or the controller 836 via the control lines 838. The air sample exhausts from the filter test equipment of the sample system through the exhaust filter 744. The exhaust filter 744 may recirculate the filtered air sample back into the facility, the housing 702, or the decontamination system 724. This process continues until the test is complete.

Advantageously, the in-situ testing of the filter is completed without decontaminating the housing 702. By not decontaminating the housing prior to testing, significant time is saves which can be utilized for operational activities of the facilities. Moreover, since the large volume of the housing, laboratory or bio-safety cabinet or other devices in the facility are not exposed to decontamination agents, the amount of decontamination agents utilized is significantly reduced.

Upon completion of the filter test, the valve assemblies 750 are actuated to the third state. In the third state, flow is prevented through the valve assembly 750 into the housing 702, while flow is provided between the decontamination system and the sample system. Selectively, the dilutor 824, aerosol generator 822, sample manifold 820 and filter test equipment of the sample system 722, and exhaust filter 744 may be exposed to the decontamination agents. The decontamination cycle may be enhanced by the optional use of at least one of a humidifier 504, flow reverser 740 or other process for compensating for low pressure regions in the test system 790 during portions of the decontamination cycle.

An operator or the controller 836 may be utilized to actuate the valve assemblies 750. In one embodiment, the third state includes having the decontamination valve 804 in an open state while the isolation valve 802 is a closed state. To decontaminate the sample system 722, the sterilization agent flows from through the decontamination valve 804 and into the one or more valve assemblies 750 into the sample system 722. The solenoid valves 818 are held in an open state or cycled open and closed. The dilutor 824, and optionally, the aerosol generator 822 are decontaminated in as described above. The isolation valve 802 remains closed thereby preventing the flow of the sterilization agent into the housing 702. The sample system 722 may circulate the sterilization agent in the same manner as the air samples. Thus, the sterilization agent flows through all of the potentially contaminated components of the sample system 722, the aerosol generator 822, and the dilutor 824 while the containment system remains in an operational state, thereby contributing to the cost effective operation of the facility. The flow of the sterilization agent may be reversed within the tubing of the sample system 722 one or more times. Additionally, or in the alternative, the control of the humidity of the sterilization agent in the sample system 722 may be eliminated through the use of the humidifier 504. The sterilization agent may be recirculated back into the decontamination system 724. The duration of the decontamination process is a function of the hazardous particles to be decontaminated. With the decontamination complete the valve assemblies 750 may return to the first state. The decontamination lines 835 can uncouple from the one or more valve assemblies 750. The decontamination system 724 and/or the sample system 722 may then be moved to another housing 702 of the same or a separate containment system 700. The process may be repeated to certify another filter.

The embodiments described herein enable HEPA and carbon filters in containment, glove box, biological safety cabinets, transfer units, isolators and other filtration systems to be certified for leaks via scan testing and/or overall efficiency testing without having to decontaminate or sterilize the housing in which the filter is installed prior to conducting filter certification. This eliminates the need to decontaminate or sterilize laboratories, work spaces, clean spaces, production areas, glove boxes, clean benches or other areas or systems serviced by the containment and filtration systems described above. This is advantageous in that it reduces facility down-time associated with having to decontaminate systems or areas listed above. Reducing the facility down time can equate to higher yields, production capacity, profitability or experiment duration. Further, the system provides a cost-effective method to certify filters after an "upset" condition without having to shut down the experiment and potentially lose months or even years worth of time, money and investment, as well as eliminating potential adverse impacts on socially critical experiments or processes.

While the foregoing is directed to embodiments of the present invention, other and further embodiments of the invention may be devised without departing from the basic scope thereof, and the scope thereof is determined by the claims that follow.

What is claimed is:

1. A method for decontaminating tubing, comprising:
    flowing a sterilization agent through a section of tubing in a first direction; and
    flowing the sterilization agent through the section of tubing in a second direction, wherein flowing the sterilization agent through the section of tubing further comprises flowing the sterilization agent through filter test equipment, wherein the filter test equipment comprises at least one of a diluter, a photometer and a particle counter.

2. The method for decontaminating tubing of claim 1 further comprising:
    soaking the sterilization agent in the section of tubing between the steps of flowing the sterilization agent through the section of tubing in the first direction and flowing the sterilization agent through the section of tubing in the second direction.

3. The method for decontaminating tubing of claim 1, further comprising:
    operating a vacuum pump to flow the sterilization agent through the section of tubing in the first direction.

4. The method for decontaminating tubing of claim 3, further comprising:
    reversing a direction of the vacuum pump to change the flow through the section of tubing from the first direction to the second direction.

5. The method for decontaminating tubing of claim 3, further comprising:
    actuating one or more valves to change the flow through the section of tubing from the first direction to the second direction, wherein the one or more valves have a first state that couples an inlet of the vacuum pump to tubing disposed in a sampling system and a second state that couples an outlet of the vacuum pump to tubing disposed in the sampling system.

6. The method for decontaminating tubing of claim 3, further comprising:
    isolating the vacuum pump from the sampling system while flowing the sterilization agent in the second direction.

7. The method for decontaminating tubing of claim 1, further comprising:
    maintaining a relative humidity level within the sampling system between about 60 to 80% RH.

8. The method for decontaminating tubing of claim 7, further comprising:
    generating the sterilization agent in a sterilization agent generator;
    separating a flow of the sterilization agent into a first stream and a second stream;
    flowing the first stream of the sterilization agent through a humidifier;

combining the first stream of the sterilization agent exiting the humidifier with the second stream of the sterilization agent to define a humidified stream of the sterilization agent; and flowing the humidified stream of the sterilization agent into the sampling system in the first direction.

9. The method for decontaminating tubing of claim 1, wherein the sterilization agent is formaldehyde or chlorine dioxide or hydrogen peroxide or mixtures of these or mixtures of one of these agents with other chemicals, gasses or vapors or their mixtures.

10. The method of claim 1 further comprising:
passing air through an air filter disposed in a housing; and
testing the air filter with the filter test equipment fluidly coupled to the housing.

11. The method of claim 10 further comprising:
flowing the sterilization agent into the housing.

12. A method for decontaminating tubing in a test system coupled to a containment system, the containment system having a containment housing having an airflow inlet aperture, an airflow outlet aperture, a bag-in/bag-out filter access port, a filter mounting portion disposed between the inlet and outlet apertures and configured to sealingly secure a filter in the containment housing in a position that filters air flowing between the inlet and outlet apertures through the containment housing, a plurality ports formed through the containment housing, wherein the ports include at least a downstream sample port and an upstream sample port coupled to the test system, the test system having at least one of a diluter, a photometer and a particle counter, components of the test system coupled by the tubing, the method comprising:
operating a vacuum pump to create a flow of sterilization agent in the test system in a first flow direction; and
reversing the flow direction of the sterilization agent in the test system.

13. The method for decontaminating tubing of claim 12 further comprising:
soaking the sterilization agent in the tubing prior to reversing the flow direction of the sterilization agent.

14. The method for decontaminating tubing of claim 12, wherein reversing the flow direction of the sterilization agent in the test system further comprising:
at least one of operating the vacuum pump in a reverse direction or isolating an inlet of the vacuum pump from the test system.

15. The method for decontaminating tubing of claim 12, wherein reversing the flow direction of the sterilization agent in the test system further comprising:
actuating one or more valves to reverse the flow of the sterilization agent through the tubing, wherein the one or more valves have a first state that couples an inlet of the vacuum pump to tubing disposed in a test system and a second state that couples an outlet of the vacuum pump to tubing disposed in the test system.

16. The method for decontaminating tubing of claim 12, further comprising:
maintaining a relative humidity level within the sampling system between about 60 to 80% RH.

17. The method for decontaminating tubing of claim 12, further comprising:
separating a flow of the sterilization agent into a first stream and a second stream prior to introduction into the test system;
flowing the first stream of the sterilization agent through a humidifier;
combining the first stream of the sterilization agent exiting the humidifier with the second stream of the sterilization agent to define a humidified stream of the sterilization agent; and
flowing the humidified stream of the sterilization agent into the sampling system in the first direction.

* * * * *